(12) United States Patent
Richard et al.

(10) Patent No.: US 9,044,197 B2
(45) Date of Patent: Jun. 2, 2015

(54) METHOD FOR X-RAY DOSE TRACKING

(71) Applicant: Carestream Health, Inc., Rochester, NY (US)

(72) Inventors: Samuel Richard, Rochester, NY (US); David H. Foos, Webster, NY (US); Lynn M. La Pietra, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 76 days.

(21) Appl. No.: 13/917,067

(22) Filed: Jun. 13, 2013

(65) Prior Publication Data

US 2014/0140477 A1 May 22, 2014

Related U.S. Application Data

(60) Provisional application No. 61/729,104, filed on Nov. 21, 2012.

(51) Int. Cl.
*G01N 23/04* (2006.01)
*A61B 6/00* (2006.01)

(52) U.S. Cl.
CPC ..................... *A61B 6/544* (2013.01)

(58) Field of Classification Search
CPC .......... H05G 1/46; A61B 6/542; A61B 6/544; G01N 23/04; G01N 23/046
USPC ........... 378/62, 65, 95, 97, 98, 108, 117, 162, 378/165
See application file for complete search history.

(56) References Cited

U.S. PATENT DOCUMENTS

| | | |
|---|---|---|
| 7,627,079 B2 | 12/2009 | Boone |
| 2007/0098140 A1 | 5/2007 | Tsujii et al. |
| 2010/0239069 A1 | 9/2010 | Bourdeaux et al. |
| 2011/0270623 A1 | 11/2011 | Reiner |
| 2012/0148132 A1 | 6/2012 | Couch et al. |
| 2012/0213326 A1 | 8/2012 | Walker et al. |
| 2012/0230470 A1 | 9/2012 | Bertram et al. |
| 2012/0300912 A1 | 11/2012 | Chung et al. |

FOREIGN PATENT DOCUMENTS

| | | |
|---|---|---|
| JP | 2008-264519 | 11/2008 |
| WO | WO 2007/014104 | 2/2007 |

OTHER PUBLICATIONS

ICRP Publication 103, The 2007 Recommendations of the International Commission on Radiological Protection (Extract), 2007, 35 pages.

*Primary Examiner* — Courtney Thomas

(57) ABSTRACT

A method for providing x-ray dose information is executed at least in part by a computer and includes obtaining two or more technique setup parameters for a pending x-ray examination for a patient, at least one dimensional distance parameter related to the x-ray system, patient information parameters identifying one or more physical characteristics of the patient, and identifying the patient anatomy that is to be exposed. The projected effective dose value are calculated and displayed according to the obtained technique setup, dimensional distance, patient information parameters, and patient anatomy information. A message is displayed to the operator related to disabling the pending x-ray examination according to the calculated projected effective dose value.

18 Claims, 6 Drawing Sheets

METHOD FOR X-RAY DOSE TRACKING

REFERENCE TO RELATED APPLICATIONS

This application claims the benefit of U.S. Provisional Patent Application Ser. No. 61/729,104 filed Nov. 21, 2012 in the names of Samuel Richard et al., the contents of which are incorporated fully herein by reference.

FIELD OF THE INVENTION

The invention relates generally to x-ray imaging and more particularly to methods for computing and reporting x-ray dose information for a patient.

BACKGROUND

Recognizing the potential hazards of ionizing radiation to various bodily organs, medical practitioners have expressed considerable interest in carefully managing the amount of x-ray radiation that is delivered to patients for radiographic imaging. Aspects of prudent management for radiation exposure include limiting the overall amount of radiation exposure when planning and carrying out each individual examination as well as tracking exposure of the patient to x-ray radiation over time. The need for this type of management, while appropriate for patients of all ages, is particularly challenging and acute for the pediatric patient population, in which patient size varies over a broad range. Patient weight, for example, can vary over a range from about 1 kg to more than 100 kg in pediatric imaging.

Calculation of exposure received by a patient is complicated by a number of factors. Different energy levels are set up in the technique used for radiography, depending on the type of examination, along with different source-to-detector (SID) and source-to-patient distances. Dose and image quality often represent a tradeoff, calling for judgement by the practitioner in setting technique parameters. Different parts of the anatomy exhibit different response to x-ray radiation, due to variations in relative density and other characteristics, and may absorb different spectral portions of the radiation received. Some organs are more sensitive to radiation than others. Patient sex, weight, and thickness are also factors that can affect the actual amount of exposure received.

Conventional approaches to the problem of exposure calculation, prediction, and tracking fall short of what is needed. For calculating the amount of exposure received by a patient in a particular examination, for example, approximation of exposure typically uses look-up tables with statistically averaged values, based on numerous assumptions about the patient and about the imaging conditions that may not be accurate. For technique setup before acquiring the x-ray image, an index or exposure level may be automatically generated or recommended, but may be inaccurate, setting parameters to levels that do not properly account for patient physiology. The resulting lack of information, or poorly set parameters, can lead to increased and unnecessary x-ray exposure. This is a particular concern for children, the most sensitive segment of the population exposed to x-ray radiation.

Thus, it can be seen that there is a need for improved methods that more accurately determine and communicate x-ray dose information and recommendations.

SUMMARY

It is an aspect of this application to address in whole or in part, at least the foregoing and other deficiencies in the related art.

It is another aspect of this application to provide in whole or in part, at least the advantages described herein.

Another aspect of this application is to provide radiographic image methods and/systems.

Aspects of the present invention address the need for improved computation and reporting of x-ray dose information for a patient. Advantageously, embodiments of the present invention calculate, use, and report dose information that more accurately characterizes dose for a particular radiographic imaging exam.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the present disclosure, there is provided a method for providing x-ray dose information, the method executed at least in part by a computer and comprises: obtaining two or more technique setup parameters for a pending x-ray examination for a patient; obtaining at least one dimensional distance parameter related to the x-ray system; obtaining patient information parameters identifying one or more physical characteristics of the patient; identifying the patient anatomy that is to be exposed; calculating and displaying a projected effective dose value according to the obtained technique setup, dimensional distance, patient information parameters, and patient anatomy information. In one embodiment, the method can comprise displaying a message to the operator related to disabling the pending x-ray examination according to the calculated projected effective dose value.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE EMBODIMENTS

The following is a detailed description of the preferred embodiments, reference being made to the drawings in which the same reference numerals identify the same elements of structure in each of the several figures. It should be noted that these figures are provided to illustrate overall functions and relationships according to embodiments of the present invention and are not provided with intent to represent actual size or scale.

Where they are used, the terms "first", "second", "third", and so on, do not necessarily denote any ordinal or priority relation, but may be used for more clearly distinguishing one element or time interval from another.

In the context of the present disclosure, the term "image" refers to multi-dimensional image data that is composed of discrete image elements. For 2-D images, the discrete image elements are picture elements, or pixels. For 3-D images, the discrete image elements are volume image elements, or voxels. The term "volume image" is considered to be synonymous with the term "3-D image".

In the context of the present disclosure, the terms "viewer", "operator", and "user" are considered to be equivalent and refer to the viewing practitioner or other person who examines an image on a display monitor. An "operator instruction" or "viewer instruction" is obtained from explicit commands entered by the viewer, such as using a computer mouse or keyboard entry.

In the context of the present disclosure, the terms "digital sensor" and "digital detector" are considered to be equivalent. These describe the panel that obtains image data in a digital radiography system.

In the context of the present disclosure, the term "effective dose" relates to a tissue-weighted sum of equivalent dose, a measure of absorbed dose, in specified tissues and organs of the body. Effective dose is quantified in sieverts (Sv).

Figure 1A:
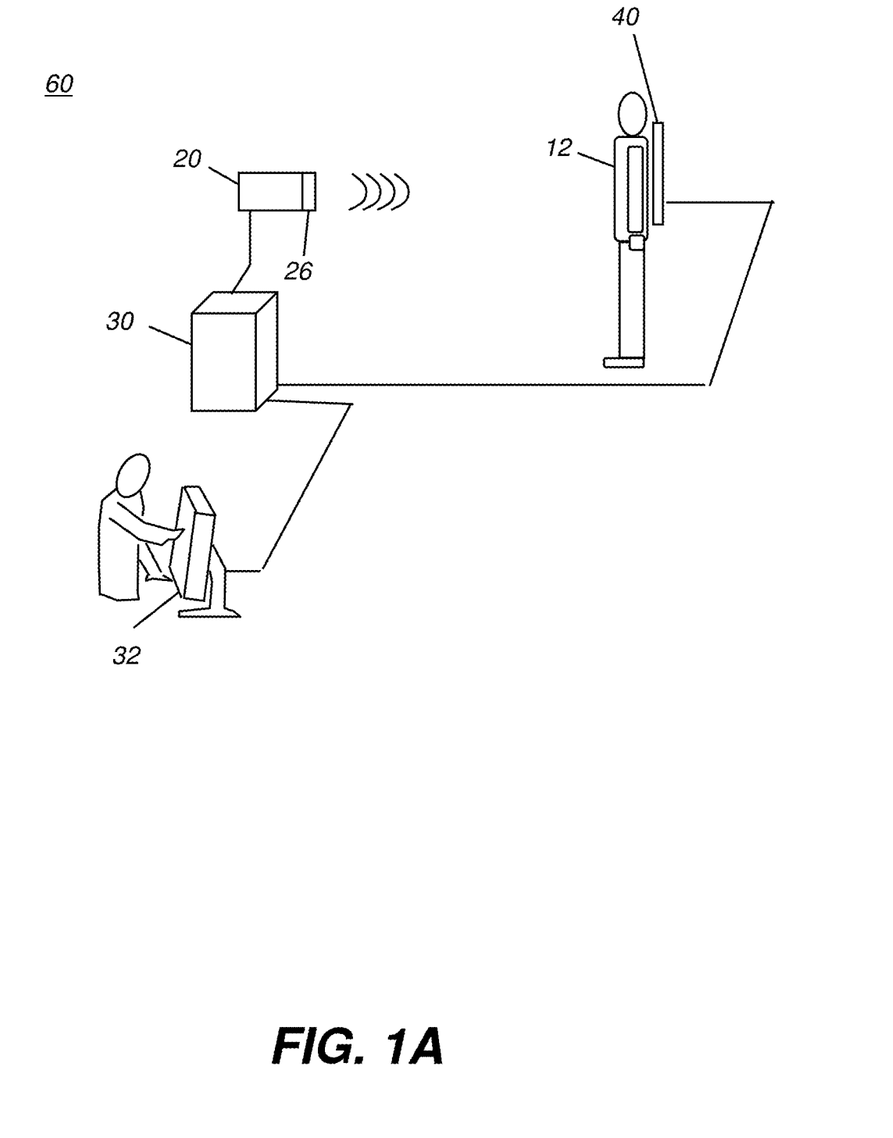
FIG. 1A is a schematic view of an imaging apparatus that executes the method of an embodiment of the present invention.

Referring to FIG. 1A, there is shown a schematic diagram of an imaging apparatus 60 for digital radiography (DR) imaging of a patient 12 or other subject according to an embodiment of the present invention. An x-ray source 20 provides the needed exposure radiation for imaging, under the control of control logic that executes on a host processor 30, such as a computer, that has an operator control console 32 for entry of setup and operation commands. X-ray source 20 has a collimator 26 that provides a variable-sized opening for controlling the distribution of radiation that is provided. Imaging apparatus 60 uses a DR detector 40 that is energizable to generate image data after receiving x-ray emission from the x-ray source.

Figure 1B:
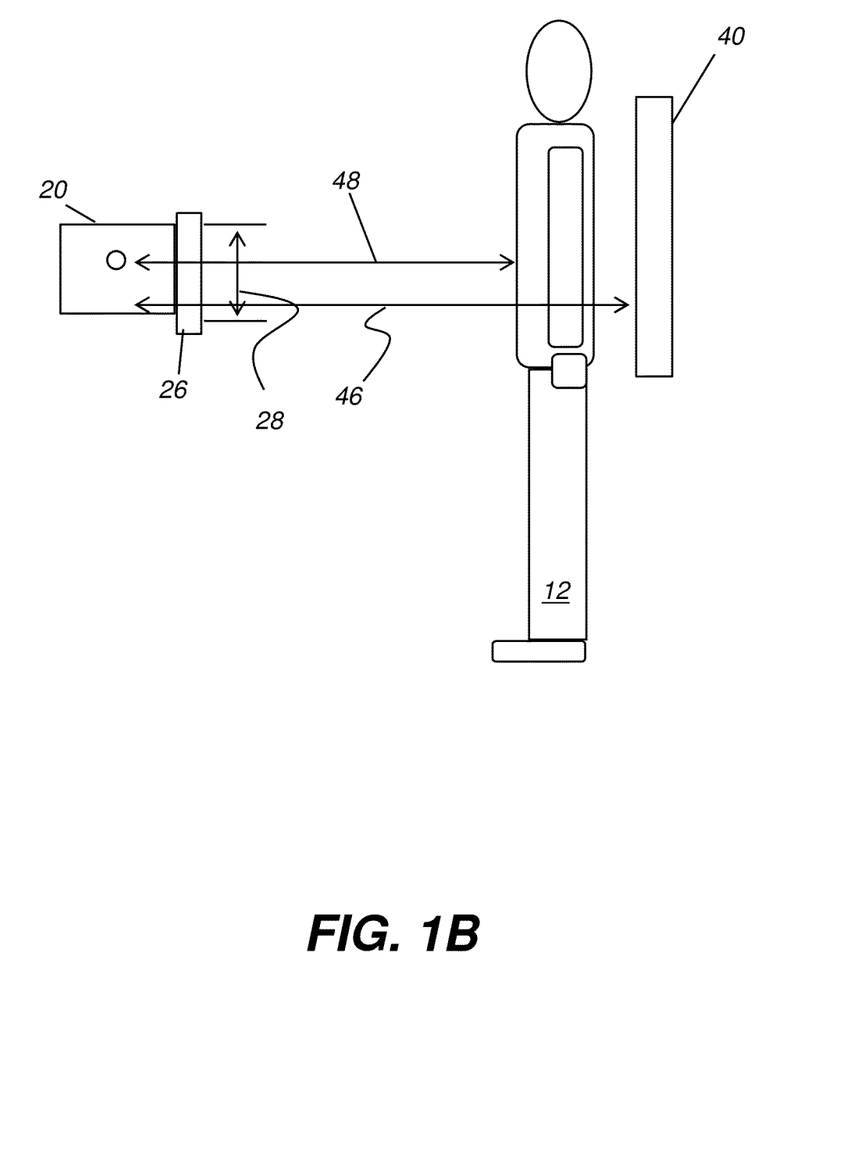
FIG. 1B shows a number of dimensions that are used for exposure calculation.

FIG. 1B shows a number of dimensional distance parameters that can relate to dosage calculation. A source-to-detector distance 46 gives the dimension from the x-ray source to detector 40. A source-to-patient distance 48, also termed a focus-to-skin distance (FSD) gives the dimension from the source to the patient 12. A collimation setting 28 gives the dimension of the collimator 26 opening setting.

Figure 2:
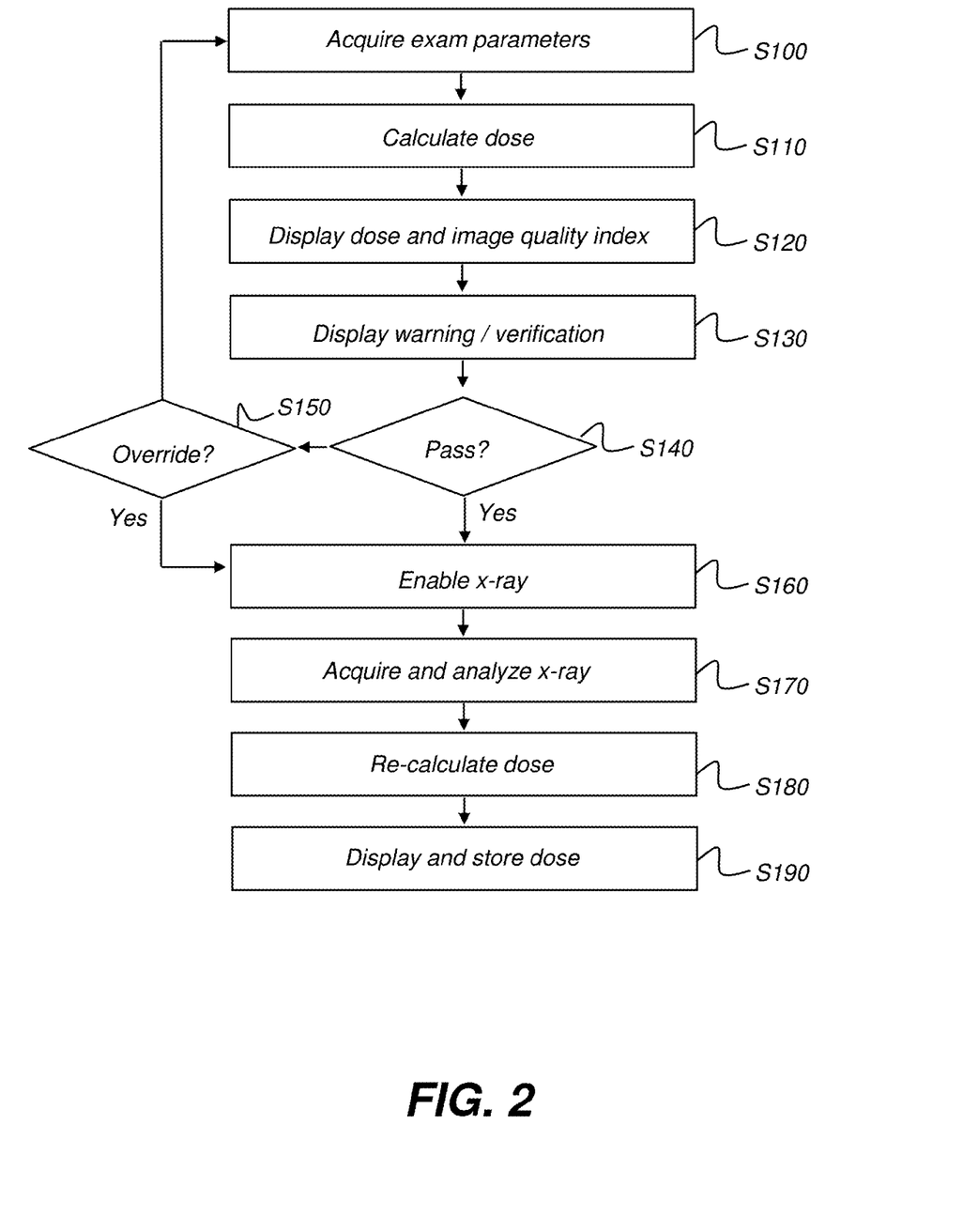
FIG. 2 is a logic flow diagram that shows a sequence of steps for dose calculation and reporting.

The logic flow diagram of FIG. 2 shows a sequence of steps for dose calculation and reporting and for controlling the enablement of the x-ray source based on the dose calculation. To begin this process, an acquire exam parameters step S100 obtains the following parameters that relate to a particular exam:

(i) two or more technique setup parameters, including exam type and kVp (peak kilovoltage) and mAs (milliampere second) values, for example;
(ii) at least one dimensional distance parameter, such as collimation setting, focus-to-skin distance, or source-to-detector distance as shown schematically in FIG. 1B;
(iii) patient information parameters, such as weight, age, sex, and thickness; and
(iv) anatomy to be exposed.

A dose calculation step S110 then calculates anticipated or projected effective dose according to the acquired exam parameters. A dose and index display step S120 displays the calculated dose value and, alternately, an index that is indicative of prospective image quality according to the dose calculations. A message display step S130 displays an optional prompt for verification of dose calculation and displays an optional warning when the dose is considered to be excessive for a given exam, based on stored guidelines used at a particular site. A test step S140 determines whether or not to allow an operator override in an override step S150 or to enable the x-ray in an enablement step S160. Enablement step S160 automatically executes where the calculated dose value is within an acceptable range. An image acquisition step S170 acquires the image data from the detector and analyzes the acquired data to determine which organs of the patient were exposed. This information then goes to a dose re-calculation step S180 that re-calculates an actual effective dose for the exposed organs. A dose display step S190 displays and stores the re-calculated dose value. The effective dose value from either or both steps S120 and S180 can be stored as DICOM (Digital Imaging and Communications in Medicine) data associated with the radiography image, for example.

Where override is not selected in step S150, execution loops back to acquire exam parameters step S100 for adjustment of alternate exam parameters or other changes to system setup.

From the logic flow diagram of FIG. 2, it can be seen that dose can be calculated both prior to image acquisition and following the actual exposure. In either case, it is useful for the dose calculations to have information on the anatomy that is to be, or has been, exposed.

According to an embodiment of the present invention, image acquisition step S170 performs a partial or coarse segmentation of anatomical features from the acquired image data in order to determine which organs have been exposed and by how much dose. Segmentation for this purpose can be done in a number of ways. According to an embodiment of the present invention, anatomical features are automatically identified using prior information such as the exam type and knowledge of the imaged anatomy for a patient of given size. The exam type indicates that at least a given set of organs is to be exposed and provides at least some information on landmark features that can be used to assist segmentation. For a chest exam, for example, features that assist in segmentation can include the left and right apex of the lungs. These provide at least benchmark information for estimating the location of other organs. Given this type of information, any of a number of types of segmentation processing can be executed. Alternately, the location of landmark features can be entered manually on the displayed image by the practitioner or organs identified using methods such as outlining or semi-automated segmentation methods, for example. According to an alternate embodiment of the present invention, keyboard entry or menu selection are used to list organs that have been or that will be exposed.

Once anatomical features and organs have been identified by some type of segmentation, the system performs an exposure calculation. For this purpose, a virtual 3D model of that patient, that is, a virtual phantom, can be used. This phantom can be mathematically modified to best approximate the patient with adjustments to account for variability in weight, height, sex, and age. According to an embodiment of the present invention, the 3D phantom with the information about the exposed area is used for a Monte-Carlo simulation which creates randomized x-ray events to simulate the interaction of x-rays with the patient's organs in order to estimate how much dose each organ received.

Various information is needed in order to compute effective dose, as defined in ICRP Publication 103, *The 2007 Recommendations of the International Commission on Radiological Protection (Extract)*, a well-known standard used to assess radiation exposure to patients. Effective dose varies with factors such as the relative sensitivity of various types of tissue to radiation. Tissue weighting factors are provided that vary according to the sensitivity of various organ types. The weighting factor for reproductive organs, for example, is several times higher than the weighting factor for bone structures.

Once the organs exposed have been identified, the system calculates the relative thickness of the patient. The patient thickness is inferred from the difference in signal levels behind the patient and "in air" signal. Alternatively the practitioner can enter the patient thickness as an input into the acquisition system, such as by entering a thickness dimension or thickness index, for example.

Optional generation of an image quality index according to technique parameters can be performed in a number of ways. According to an embodiment of the present invention, the image quality index is computed statistically, based on a population of images obtained for patients having different characteristics and over a range of technique parameters. It should be noted that image quality, since it is in part a result of energy level settings and other technique factors, is indirectly related to dose.

Figure 3:
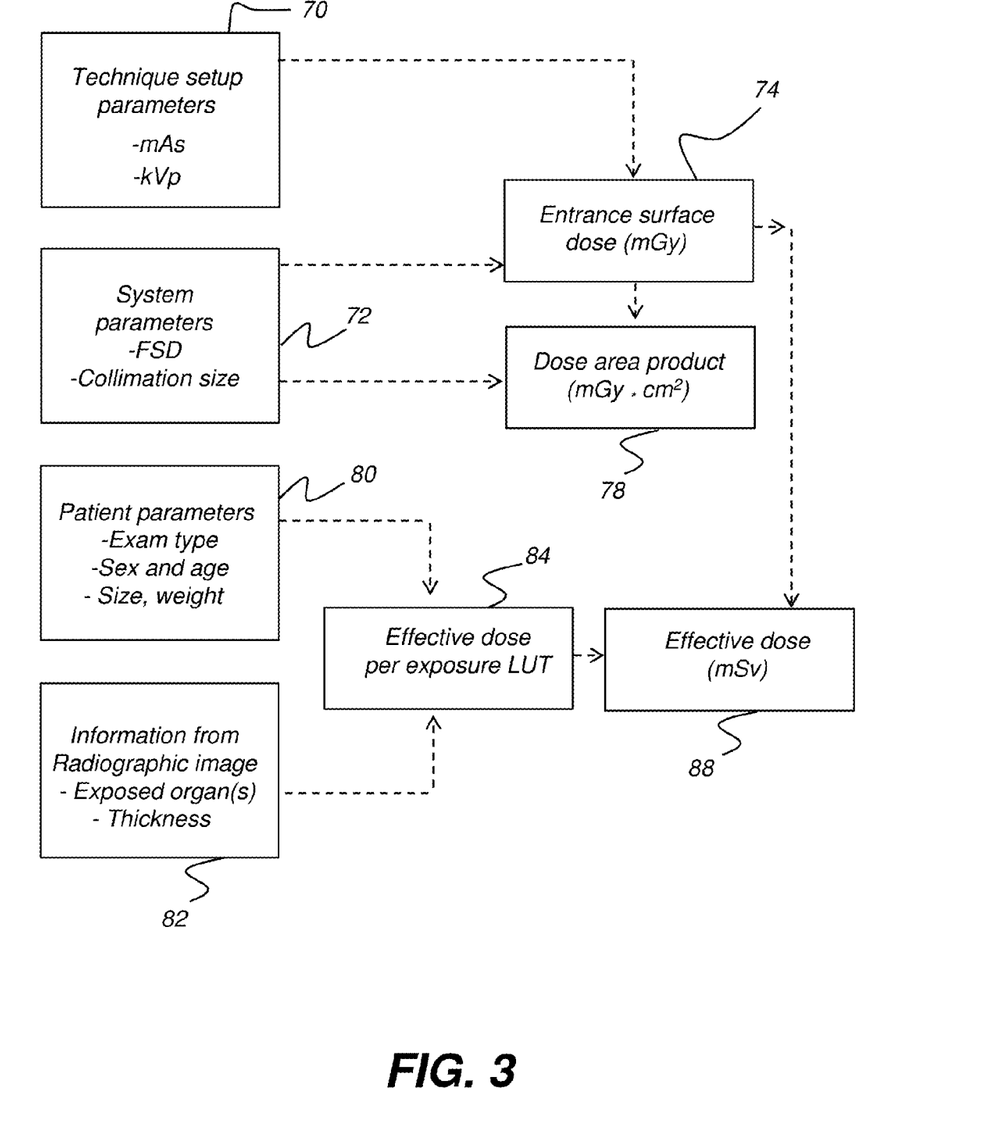
FIG. 3 is a logic flow diagram that shows the factors used and calculations performed for dose calculation.

The logic flow diagram of FIG. 3 shows the factors used and calculations performed for dose calculation step S110 and for dose re-calculation step S180 of FIG. 2 according to an embodiment of the present invention. Technique setup parameters 70 and system parameters 72 such as focus to skin distance (FSD) and filtration are used to calculate exposure at the skin surface, generating a value for entrance surface dose 74. Collimation size from system parameters 72 is combined with entrance surface dose 74 to generate a dose area product 78. Patient parameters 80 including exam type, patient sex and age, weight, and other data are then combined with information from the x-ray image 82 and, optionally, from automated segmentation or operator markup, to determine which anatomy or organs of the patient were exposed. This information is used in a look-up table (LUT) 84 or in some other transformation or reference look-up data for calculating an effective dose 88. A different effective dose value can be generated and stored for each exposed organ. For the dose estimate of dose calculation step S110, simulation is performed using a virtual phantom that is generated according to the obtained system, patient, and exam parameters.

The generation and use of a virtual phantom is known to those skilled in the radiography analysis arts. Typically, a large number of exposures are obtained at different energy levels from phantoms of various densities. This density information is correlated to the densities of different patient organs and, where needed, interpolation is used in order to provide a close approximation of how much exposure is obtained in imaging.

Figure 4:
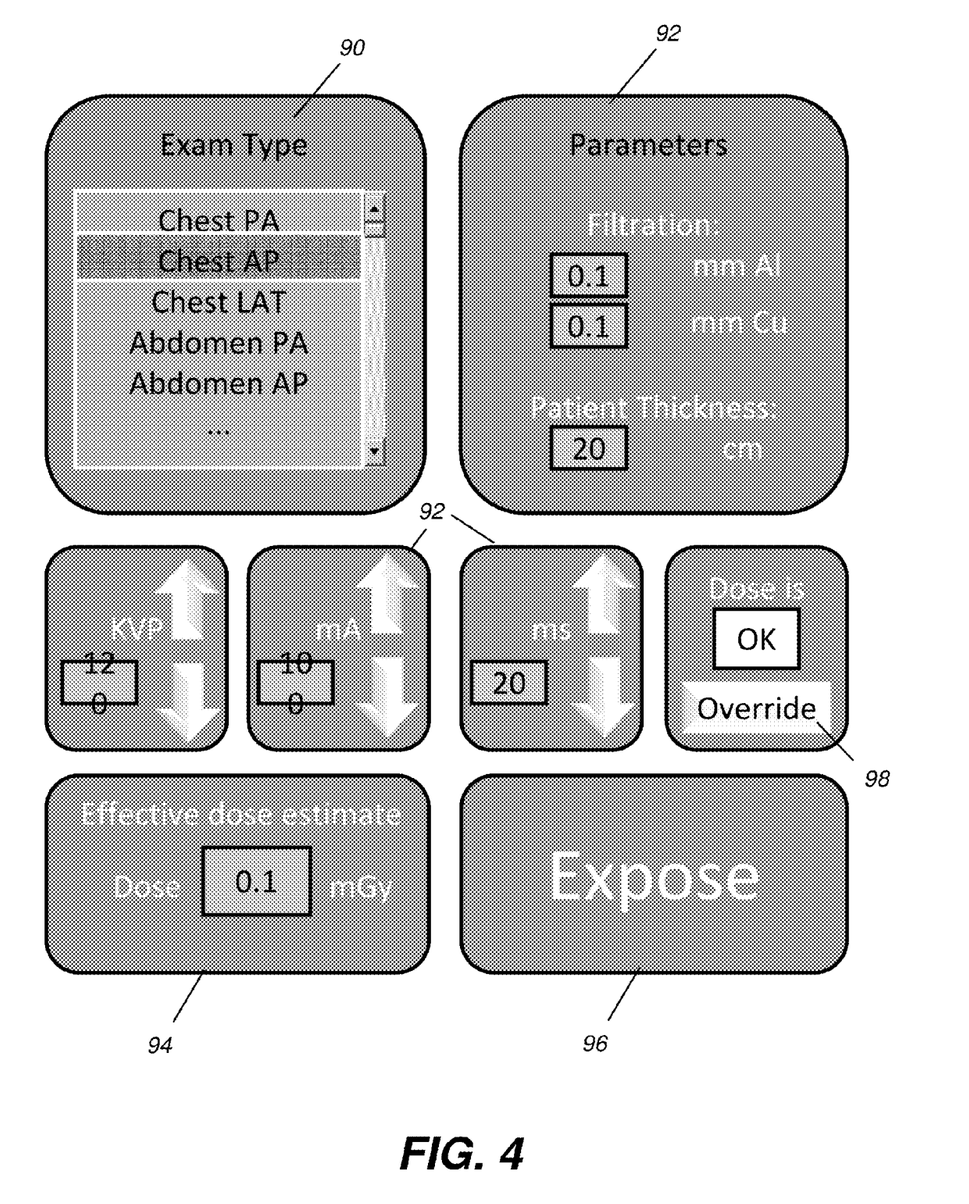
FIG. 4 shows elements of an operator interface on a control console for an x-ray imaging apparatus according to an embodiment of the present invention.

The plan view of FIG. 4 shows elements of an operator interface for obtaining an image based on exposure computation. An exam type field 90 lists the exam type specified by an operator. One or more parameters fields 92 then list various parameters that can be set by the operator or can be modified according to operator adjustment. Parameters fields 92 are set according to specific parameters for the exam. A dose estimate field 94 lists the latest available effective dose estimate for the given parameter settings, with consideration for which organs are to be exposed. An expose control 96 allows the operator to initiate x-ray exposure. An override control 98 enables the operator to override system disablement of the exposure mechanism due to a high effective dose estimate. This estimate may be compared against dose thresholds used at a particular hospital or other facility to determine whether override applies.

Figure 5:
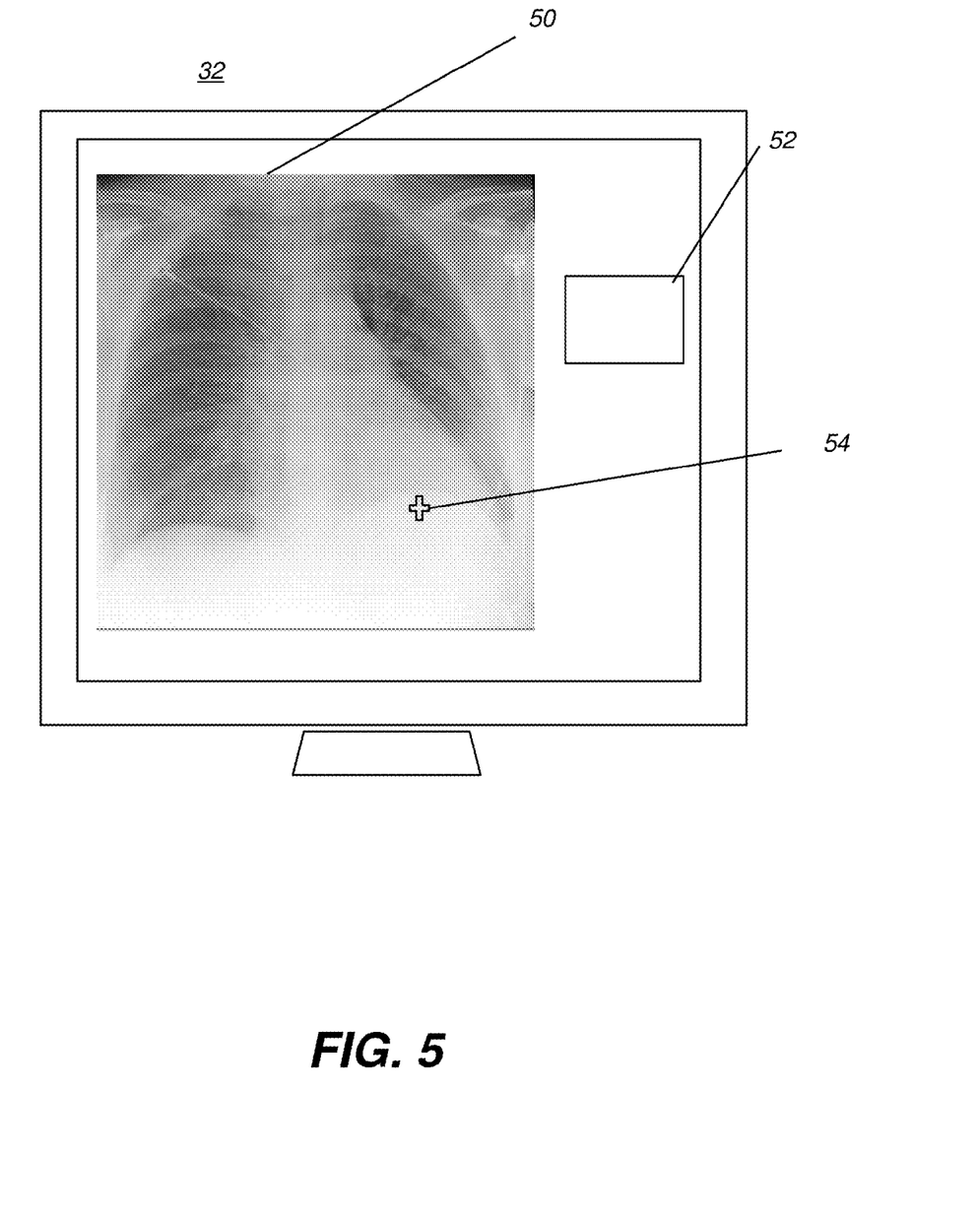
FIG. 5 shows an operator interface on a control console that displays a radiographic image obtained from an imaging apparatus and showing exposure values.

FIG. 5 shows an operator interface on control console 32 that displays a radiographic image 50 obtained from imaging apparatus 60. A displayed exposure value 52 responds to position of a cursor 54 by indicating the effective dose value that has been computed for the organ or type of tissue at the cursor 54 position. Moving cursor 54 to a different organ or tissue type causes a corresponding change to the displayed exposure value 52. According to an alternate embodiment of the present invention, one or more segmented organs can be individually displayed along with their corresponding dose value. According to yet another alternate embodiment of the present invention, a table or other text listing displays and shows predicted or computed exposure values, by organ or tissue type.

According to one aspect of the present disclosure, there is provided a method for display of exposure values computed for at least first and second organs within a radiographic image, the method executed at least in part by a computer and comprising: acquiring the radiographic image; segmenting the image to identify the at least the first and second organs; processing the radiographic image to calculate a first effective dose value for the first organ and to calculate a second effective dose value for the second organ; and displaying the first effective dose value when a screen cursor is at the position of the first organ in the image and displaying the second effective dose value when the screen cursor is at the position of the second organ in the image.

Consistent with an embodiment of the present invention, a computer executes a program with stored instructions that perform on image data accessed from an electronic memory. As can be appreciated by those skilled in the image processing arts, a computer program of an embodiment of the present invention can be utilized by a suitable, general-purpose computer system, such as a personal computer or workstation, as well as by a microprocessor or other dedicated processor or programmable logic device. However, many other types of computer systems can be used to execute the computer program of the present invention, including networked processors. The computer program for performing the method of the present invention may be stored in a computer readable storage medium. This medium may comprise, for example; magnetic storage media such as a magnetic disk (such as a hard drive) or magnetic tape or other portable type of magnetic disk; optical storage media such as an optical disc, optical tape, or machine readable bar code; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other communication medium. Those skilled in the art will readily recognize that the equivalent of such a computer program product may also be constructed in hardware.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

It should be noted that the term "memory", equivalent to "computer-accessible memory" in the context of the present disclosure, can refer to any type of temporary or more enduring data storage workspace used for storing and operating upon image data and accessible to a computer system. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing processes and for recording entered values, such as seed points, or storing intermediate and final results of calculations and other processing. Computer-accessible memory can be volatile, non-volatile, or a hybrid combination of volatile and non-volatile types. Computer-accessible memory of various types is provided on different components throughout the system for storing or recording, processing, transferring, and displaying data, and for other functions.

The invention has been described in detail, and may have been described with particular reference to a suitable or presently preferred embodiment, but it will be understood that variations and modifications can be effected within the spirit and scope of the invention. In addition, while a particular feature of the invention can have been disclosed with respect to at least one of several implementations/embodiments, such feature can be combined with one or more other features of the other implementations/embodiments as can be desired or advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Further, "exemplary" indicates the description is used as an example, rather than implying that it is an ideal. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for providing x-ray dose information, the method executed at least in part by a computer and comprising:
   obtaining two or more technique setup parameters for a pending x-ray examination for a patient;
   obtaining at least one dimensional distance parameter related to an x-ray system;
   obtaining patient information parameters identifying one or more physical characteristics of the patient;
   identifying the patient anatomy that is to be exposed;
   calculating and displaying a projected effective dose value according to the obtained technique setup, dimensional distance, patient information parameters, and patient anatomy information;
   and
   displaying a message to the operator related to disabling the pending x-ray examination according to the calculated projected effective dose value.

2. The method of claim 1 wherein the two or more technique parameters are a kVp value and an mAs value.

3. The method of claim 1 wherein the at least one dimensional distance parameter relates to one or more of a collimator opening distance, a source-to-detector distance, and a source-to-patient distance.

4. The method of claim 1 wherein the patient information parameters further comprise a thickness value for patient anatomy.

5. The method of claim 1 further comprising providing an override selection for acquiring a radiographic image for the patient.

6. The method of claim 1 further comprising obtaining a radiographic image and identifying at least one organ exposed to radiation from the obtained radiographic image.

7. The method of claim 6 further comprising computing and displaying an actual absorbed dose value for the at least one organ.

8. The method of claim 7 further comprising computing and displaying an actual effective dose value for the patient.

9. A method for providing x-ray dose information, the method executed at least in part by a computer and comprising:
   obtaining two or more technique setup parameters for a pending x-ray examination for a patient;
   obtaining at least one dimensional distance parameter related to the x-ray system;
   obtaining patient information parameters identifying at least the patient age, sex, and weight;
   calculating and displaying a projected effective dose value according to at least the two or more obtained technique setup parameters, the at least one obtained dimensional distance parameter, and the patient information parameters;
   accepting an operator command acknowledging the calculated projected effective dose value;
   acquiring a radiographic image of patient anatomy according to the at least the two or more obtained technique setup parameters, the at least one obtained dimensional distance parameter, and the patient information parameters;
   segmenting at least a portion of the patient anatomy within the acquired radiographic image; and
   generating and displaying a re-calculated effective dose value according to the at least the portion of the segmented patient anatomy within the acquired radiographic image.

10. The method of claim 9 wherein the at least the portion of the segmented patient anatomy for the re-calculated effective dose value applies to a first organ.

11. The method of claim 10 wherein the re-calculated effective dose value for the first organ is a first re-calculated effective dose value and wherein there is further a second re-calculated effective dose value for a second organ of the segmented patient anatomy.

12. The method of claim 10 wherein segmenting the patient anatomy further comprises identifying one or more organs in the radiographic image.

13. The method of claim 9 further comprising calculating a thickness value for the patient according to radiographic image data.

14. A method for providing x-ray dose information for an obtained radiographic image of a patient, the method executed at least in part by a computer and comprising:

obtaining two or more technique setup parameters used to generate the obtained radiographic image;

obtaining at least one dimensional distance parameter related to the x-ray system in generating the image;

identifying one or more patient organs exposed in the image; and calculating and displaying an absorbed dose value for each of the one or more identified patient organs according to at least the two or more obtained technique setup parameters and the at least one obtained dimensional distance parameter.

15. The method of claim 14 wherein displaying the absorbed dose value comprises responding to the position of a cursor over the image and displaying the absorbed dose value for the identified organ of the patient that corresponds to the cursor position.

16. The method of claim 14 further comprising calculating and displaying an effective dose for the patient according to at least the two or more obtained technique setup parameters and the at least one obtained dimensional distance parameter.

17. The method of claim 14 further comprising segmenting the obtained radiographic image to identify the one or more organs of the patient that have been exposed.

18. The method of claim 14 further comprising obtaining one or more patient information parameters, where the calculating and displaying the absorbed dose value for each of the one or more identified patient organs and an effective dose for the patient is according to the obtained one or more patient information parameters.

\* \* \* \* \*